United States Patent
Johnson et al.

(10) Patent No.: US 6,503,490 B2
(45) Date of Patent: Jan. 7, 2003

(54) DEODORANT PRODUCTS

(75) Inventors: Paula Ann Johnson; Andrew Sjaak Landa; Stephen Anthony Makin; Victoria Anne McKay, all of Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/973,343

(22) Filed: Oct. 9, 2001

(65) Prior Publication Data

US 2002/0065249 A1 May 30, 2002

(30) Foreign Application Priority Data

Oct. 9, 2000 (GB) .............................................. 0024689

(51) Int. Cl.$^7$ .............................. A61K 7/32; A61K 7/00; A01N 25/00
(52) U.S. Cl. ......................... 424/65; 424/401; 424/405; 424/DIG. 5
(58) Field of Search ........................ 424/65, 400, 401, 424/405, DIG. 5

(56) References Cited

U.S. PATENT DOCUMENTS 3,507,796 A    4/1970   Voss ........................... 252/106
3,984,535 A   10/1976   Ghilardi et al. ................ 424/47
4,078,050 A    3/1978   Hart ............................. 424/76

FOREIGN PATENT DOCUMENTS

| EP | 629 347 | 12/1994 |
| EP | 979 644 | 2/2000 |
| GB | 858030 | 1/1961 |
| GB | 1 420 946 | 1/1976 |
| WO | 97/02010 | 1/1997 |
| WO | 00/70004 | 11/2000 |

OTHER PUBLICATIONS

GB Search Report in a GB application GB 0024689.2.

PCT International Search Report in a PCT application PCT/EP 01/11434.

*Primary Examiner*—Shelley A. Dodson
(74) *Attorney, Agent, or Firm*—Kevin J. Stein

(57) ABSTRACT

The invention concerns the achievement of a deodorancy benefit upon the human body or upon articles worn in close proximity thereto and involves the application of an anti-microbial product comprising a transition metal chelator and a phenolic or enolic compound that is (a) a transferrin dissociation promoter that operates by aiding the reduction of iron(III) bound to transferrin to iron(II) and/or (b) an anti-oxidant comprising a tert-butylphenol group.

21 Claims, No Drawings

DEODORANT PRODUCTS

FIELD OF INVENTION

This invention relates to the field of anti-microbial and deodorant compositions. In addition, this invention is concerned with achieving a deodorancy benefit upon the surface of the human body and in close environs thereto. The compositions and methods involved utilise transition metal chelators and particular phenolic or enolic compounds. When used on the human body, the compositions and methods of the invention are generally of greatest benefit when used on the most malodorous areas of the body, for example the underarm areas or feet.

BACKGROUND

Anti-microbial and deodorant compositions may function by a variety of means. When used upon the human body, such compositions may function by significantly reducing microbial numbers either by reducing perspiration or by directly affecting the micro-organisms on the body surface as represented by skin. It is with this latter mechanism of action that this invention is largely concerned.

Most anti-microbial and deodorant compositions reduce the number of viable micro-organisms on the surface of the skin. It is well known that sweat is usually odourless until it has been degraded by the skin microflora. Typical deodorants include ethanol and triclosan (2,4,4'-trichloro,2'-hydroxy-diphenyl ether) which is a well known anti-microbial agent. However, the deodorising effect obtained with such deodorants wears off with the passage of time and the microflora progressively recover their numbers. There is, therefore, a continuing requirement for effective and long lasting deodorant compositions on the market. Hence, the problem to be solved is not simply reducing microbial numbers on the body surface; equally important is maintaining low microbial numbers (particularly low bacterial numbers) on the body surface (particularly in the most malodorous areas, eg. the axillae).

Deodorant compositions comprising chelators are described in our recent British patent applications GB 0001133.8, GB 0001132.0, GB 0001131.2, GB 0001130.4, and GB 0001129.6, all of which are incorporated herein by reference. These patent applications disclose the hypothesis that certain chelators can effectively inhibit the up-take of essential transition metal ion nutrients by microbes on the skin surface, thereby minimising their growth. Other references to deodorant compositions comprising transition metal chelating agents are given in these patent applications, the most relevant of which are detailed below.

U.S. Pat. No. 4,356,190 (Personal Products Co.) discloses the use of selected aminopolycarboxylic acid compounds for inhibiting the formation of short chain fatty acids by Corynebacterium on the skin surface.

WO 97/02010 (Procter and Gamble Co.) discloses the use of chelators selected from the succinic acid, glutaric acid, and phosphonic acid classes as bactericidal compounds.

WO 97/44006 (Ciba Speciality Chemicals Holding, Inc.) claims the use of nitrogen—containing complexing agents for the anti-microbial treatment of the skin and of textile fibre materials.

WO 97/01360 (Concat Ltd.) claims a method of inhibiting bacterial growth using particular substituted polyaza chelator compounds.

In the course of the present investigations, we have observed that particularly long-lasting malodour control is maintained by the combined use of a transition metal chelator and a phenolic or enolic transferrin dissociation promoter.

The presence of transferrin in mammalian sweat, including human sweat, is well-established (see, for example, S. E. Lind, *Corros. Sci.,* 1972, 12(9), 749). It is also known that certain bacteria make use of the iron bound to transferrin by means of sophisticated iron-scavenging systems including siderophores and cell surface receptors for transferrin (E.Griffiths and P.Williams, *The Iron Uptake Systems of Pathogenic Bacteria, Fungi and Protozoa in Iron and Infection* (editors: S. S.Bullen and E.Griffiths), $2^{nd}$ Edn., 1999, John Wiley and Sons, pp 87–212). Certain chemical agents, in addition to bacterial siderophores, are capable of promoting the liberation of iron from transferrin and it is with the use of particular transferrin dissociation promoters of this type that this invention is largely concerned. In particular, this invention is concerned with phenolic or enolic transferrin dissociation promoters that operate by aiding the reduction of iron(III) bound to transferrin to iron(II), which binds less strongly to transferrin (see N.Kojima and G. W.Bates, *J. Biol. Chem.,* 1979, 254(18), 8847).

Certain transition metal chelators and particular agents that can serve as transferrin dissociation promoters are disclosed in prior documents as preservative/antioxidant systems for cosmetic compositions. However, the amounts disclosed are typically very small and, in addition, the transferrin dissociation promoters disclosed in these documents are not recognised as such. A typical example is EP 979,644 (ITBR-N) which discloses a deodorant composition comprising 0.05% butylated hydroxytoluene (BHT) and 0.05% disodium ethylenediaminetetraacetic acid ($Na_2$EDTA).

SUMMARY OF THE INVENTION

We have surprisingly discovered that by the combined use of effective amounts of a transition metal chelator and particular phenolic or enolic compounds, excellent anti-microbial benefits and deodorancy benefits can be achieved.

Thus, according to a first aspect of the present invention, there is provided a method of achieving an anti-microbial and deodorancy benefit comprising the application to the human body or to an article wearable in close proximity thereto, of an anti-microbial product comprising effective amounts of a transition metal chelator and a phenolic or enolic compound that is (a) a transferrin dissociation promoter that operates by aiding the reduction of iron(III) bound to transferrin to iron(II) and/or (b) an anti-oxidant comprising a tert-butylphenol group.

In the above aspect of the present invention, 'effective amounts' refer to amounts that are sufficient for a significant deodorancy benefit to be observed 24 hours after application of the anti-microbial product. 'Application' involves deposition of both of the active components upon the substrate being treated.

According to a second aspect of the present invention, there is provided an anti-microbial deodorant composition for use on the human body comprising at least 0.35% by weight of a transition metal chelator and at least 0.05% by weight of a phenolic or enolic compound that is (a) a transferrin dissociation promoter that operates by aiding the reduction of iron(III) bound to transferrin to iron(II) and/or (b) an anti-oxidant comprising a tert-butylphenol group, wherein the weight percentages exclude any volatile propellant present.

According to a third aspect of the present invention, there is provided a method for the manufacture of a deodorant composition for use on the human body, comprising the formation of a mixture of at least 0.35% by weight of a transition metal chelator and at least 0.05% by weight of a phenolic or enolic compound that is (a) a transferrin dissociation promoter that operates by aiding the reduction of iron(III) bound to transferrin to iron(II) and/or (b) an antioxidant comprising a tert-butylphenol group, wherein the weight percentages exclude any volatile propellant present.

DETAILED DESCRIPTION

Excellent anti-microbial and deodorancy benefits are found on combined use of a transition metal chelator and a phenolic or enolic compound as described herein. Without wishing to be bound by theory, it is hypothesised that the transition metal chelator contributes to the benefits attained by inhibiting the up-take of essential transition metal ion nutrients, in particular iron(III), by microbes on the skin surface, thereby minimising their growth. It is further hypothesised that the phenolic or enolic compound contributes by interfering with biochemical pathways by which microbes on the skin surface extract iron(III) from the human iron carrier protein complex transferrin.

In employing a method according to the first aspect of this invention, it is not essential that the transition metal chelator and the phenolic or enolic compound are part of the same composition. The anti-microbial and deodorancy benefit derived from use of the invention may be gained by independent application of the chelator and the phenolic or enolic compound. Such application may be concurrent or consecutive, provided that the treated substrate experiences the presence of both components at the same time. When the components are applied from independent compositions, it is preferred that the product also comprises a means for, and/or instruction for, both of the compositions to be applied to the human body.

It is preferred that the transition metal chelator and the phenolic or enolic compound are both applied from the same composition.

The method of controlling malodour offered by the present invention is particularly useful because the benefit can extend for many hours, for example 10 hours, 24 hours, or even longer, after application of the product. This can represent an extended deodorancy benefit; that is to say, extended inhibition of the generation of odour on the human body or closely associated articles.

As stated above, articles wearable in close proximity to the human body may also be protected from malodour generation by the present invention. Such articles include any garments worn next to the skin, for example stockings and socks, and also shoes and other items of footwear.

The transition metal chelator and the phenolic or enolic compound may be present in the composition or compositions of the invention in any form. For example, either or both of the agents may be used neat or may be diluted with a volatile propellant and used as an aerosol; with an additional liquid and used, for example, as a roll-on or squeeze-spray product; or with a carrier liquid and a thickener or structurant and used, for example, as a cream, gel, soft solid, or solid stick product.

The method of achieving an anti-microbial and deodorancy benefit of the present invention is most efficacious when it comprises application of the anti-microbial product to the human body.

The anti-microbial product of the invention may be applied to the human body by any means. Application of liquid compositions may be by absorption onto a carrier matrix like paper, fabric, or sponge and application by contacting said carrier matrix with the surface of the body. Solid or semi-solid compositions may be applied by direct contact or may be dissolved or dispersed in a liquid medium prior to application. Application may also comprise a combination of any two or more of the above techniques.

Transition Metal Chelators

Preferred transition metal chelators are acids or salts with anions that have affinity for iron (III), preferably high affinity for iron (III); that is to say, a binding constant for iron (III) of greater than $10^{10}$, or, for optimum performance, greater than $10^{26}$. The 'iron (III) binding constant' referred to above is the absolute stability constant for the chelator-iron (III) complex. Such values are independent of pH and consider only the most anionic, fully deprotonated form of the chelator. Measurements can be made potentiometrically, and in a number of other ways. Full details of suitable methods can be found in "Determination and Use of Stability Constants", A. E.Martell and R. J.Motekaitis (VCH, New York, 1989). Tables of applicable values may be found in numerous sources, for example "Critical Stability Constants", R. M.Smith and A. E.Martell (Plenum Pub. Corp., 1977).

The chelators used in the present invention preferably have acid forms with at least two ionisable acid groups. The acid groups are preferably carboxylic and/or phosphonic, but may be sulphonic or phosphinic, or any mixture of these groups.

Preferred chelators with phosphonic acid groups are, in the acid form, diethylenetriaminepenta(methylphosphonic) acid (DTPMP), ethanehydroxydiphosphonic acid (EHDP), ethylenediaminetetra(methylenephosphonic acid) (EDTMP), and hexamethylenediaminetetra (methylenephosphonic acid) (HMDTMP).

Preferred chelators with carboxylic acid groups are aminopolycarboxylate compounds. The acid forms of preferred aminopolycarboxylate compounds include ethylenediaminetetraacetic acid (EDTA), trans-1,2-diaminocyclohexane-N,N,N',N'-tetraacetic acid (CDTA), and ethylenediaminedisuccinic acid (EDDS). More preferred aminopolycarboxylate chelators have the acid forms diethylenetriaminepentaacetic acid (DTPA), triethylenetetraaminehexaacetic acid (TTHA), and ethylenebis[2-(2-hydroxyphenyl)glycine] (EDDHA).

Particularly preferred chelators are able to significantly inhibit the growth of the micro-organism Staphlococcus epidermidis when present at a concentration of $3 \times 10^{-6}$ mol.dm$^{-3}$ or less. Inhibition is considered significant when growth of the S. epidermidis on a supporting medium can be reduced by at least 30%, preferably by at least 45%. A test suitable for determining the extent of inhibition of growth of S. epidermidis is given in the Examples. DTPA and TTHA are chelators capable of achieving significant inhibition; however, EDTA and CDTA are not.

The chelators preferably have only moderate molecular weight, by which it is meant that the chelators, in their acid forms, have a molecular weight of less than 1000, more preferably 200 to 800, and most preferably 290 to 580, and in their salt form have a molecular weight of less than 2000, more preferably 300 to 1400, and most preferably 500 to 1000.

The nature of the cations associated with the chelator anions is very important with regard to composition homogeneity and stability. It is preferred that the chelators possess organic cations. The chelator salts may be the result of complete or partial neutralisation of the chelator acid groups by an organic base. Also included are salts where the chelator acid groups are partially neutralised with an organic base and partially neutralised with an inorganic base, although it is preferred that such salts have at least 40% of their available acid groups neutralised by the organic base.

Suitable organic cations are protonated or quaternised amines. Salts formed using aliphatic amines are preferred to those formed from aromatic amines. It is further preferred that the amines used to form the chelator salts are relatively hydrophobic, possessing at least one N-substituent comprising a $C_1$-$C_{10}$ terminal hydrocarbyl group.

Herein, hydrocarbyl groups are radicals comprising solely carbon and hydrogen atoms.

Preferred protonated or quaternised amine cations of the chelator salts are of formula $R^1R^2R^3R^4N^{(+)}$, wherein $R^1$ is H or $CH_3$; $R^2$, $R^3$, and $R^4$ are each independently H or an aliphatic or aromatic substituent containing 0 to 3 hydroxyl groups, optionally interrupted and/or substituted by functional groups such as ether, amine, ester, or amide; with the provisos that at least one of $R^2$, $R^3$, or $R^4$ comprises a $C_1$-$C_{10}$ terminal hydrocarbyl group, optionally $R^2$ and $R^3$ together forming a ring as the terminal hydrocarbyl group.

Of the aforementioned preferred transition metal chelators of formula $R^1R^2R^3R^4N^{(+)}$, particularly preferred are transition metal chelators having cations characterised in that at least one of $R^2$, $R^3$, or $R^4$ comprises an H atom directly attached to an N atom or an O atom. The presence of an H atom directly attached to an O atom (ie. a hydroxyl group) in at least one of $R^2$, R, or $R^4$ is especially preferred, up to the aforementioned limit of 3 hydroxyl groups per N-substituent.

Other particularly preferred transition metal chelator salts have cations comprising N-substituents ($R^1$, $R^2$, $R^3$, and $R^4$, according to the formula) that collectively contain a total of 0 to 3 hydroxyl groups, preferably 0 to 2 hydroxyl groups.

In many desirable chelator salts, each N-substituent ($R^1$, $R^2$, $R^3$, and $R^4$, according to the formula) contains not more than one hydroxyl group.

Particularly preferred chelator salts have cations that are protonated aliphatic amines, for example salts of isopropanolamine, 2-amino-2-ethyl-1,3-propanediol, 2-(N,N-dimethylamino)-2-methyl-1-propanol and N,N-dimethylaminoethanol. Especially preferred are the salts of 2-amino-2-methyl-1-propanol (AMP), diisopropanolamine, 2-aminobutan-1-ol, and cyclohexylamine.

The transition metal chelator is preferably used at a level of at least 0.35% by weight of the composition of which it is a part, excluding any volatile propellant also present. In particular, the chelator is used at a level of 0.45% to 7% and especially at a level of 0.65% to 5% by weight of the composition in which it is present, excluding any volatile propellant also present. Mixtures of chelators may also be used.

Phenolic or Enolic Compound

The phenolic or enolic compound is (a) a transferrin dissociation promoter that operates by aiding the reduction of iron(III) bound to transferrin to iron(II) and/or (b) an anti-oxidant comprising a tert-butylphenol group. Materials that pass the following test are compounds of class (a):

2.7 g.$l^{-1}$ human diferric transferrin (ex Sigma Chemicals) is incubated at 37° C. in 50 mM HEPES (N-[2-hydroxyethyl]piperazine-N-[2-ethanesulfonic acid]) buffer adjusted to pH 6.5 with sodium hydroxide, together with 0.115 g.$l^{-1}$ FerroZine (ex Sigma Chemicals; 3-(2-pyridyl)-5,6-bis(4-phenylsulfonic acid)-1,2,4-triazine, monosodium salt) and 10 mmol.$l^{-1}$ of the test material, if water soluble, or 2.5 g.$l^{-1}$ of the test material, added as a finely ground powder, if water insoluble.

After 24 hours, the extent of transferrin dissociation is estimated by eye or spectrophotometrically. Transferrin dissociation promoters lead a purple colouration; in particular, they lead to an absorption at 562 nm of 0.15 or greater. This purple colouration is the result of the production of iron(II) tri(FerroZine) complex. The molar concentration of this complex is equal to the molar concentration of iron dissociated from the transferrin.

Preferred water-soluble transferrin dissociation promoters according to the invention are: ascorbic acid (and salts thereof), sodium ascorbyl phosphate, Tocophersolan, protocatechuic acid (and salts thereof), salicylic acid (and salts thereof), Tiron (4,5-dihydroxy-1,3-benzenedisulfonic acid). Preferred water-insoluble materials are ascorbyl-6-palmitate, eugenol, ferulic acid (and salts thereof), thymol, Trolox (6-hydroxy-2,5,7,8-tetramethylchroman—2-carboxylic acid) (and salts thereof), tocopherol, BHA (butylated hydroxyanisole) and BHT (butylated hydroxytoluene). Particularly preferred transferrin dissociation promoters according to the invention comprise a tert-butylphenol group.

Preferred phenolic or enolic compounds that comprise a tert-butylphenol group are compounds comprising a phenol group having two tert-butyl substituents, for example BHT, 2,2'-ethylidenebis(4,6-di-tert-butylphenol), and pentaerythritol tetrakis(3-(3,5-di-tert-butyl-4-hydroxyphenyl) propionate).

Particularly preferred phenolic or enolic compounds are ascorbic acid (and salts thereof), ascorbyl-6-palmitate, BHT, 2,2'-ethylidenebis(4,6-di-tert-butylphenol), and pentaerythritol tetrakis(3-(3,5-di-tert-butyl-4-hydroxyphenyl) propionate). BHT, is especially preferred.

The phenolic or enolic compound is preferably used at a level of at least 0.05% by weight of the composition of which it is a part, excluding any volatile propellant also present. It is also preferred that the level of use is less than 5% by weight of the composition of which it is a part, excluding any volatile propellant also present. In particular, the phenolic or enolic compound is used at a level of 0.075% to 2.5% and especially at a level of 0.1% to 1% by weight of the composition in which it is present, excluding any volatile propellant also present. Mixtures of phenolic or enolic compounds may also be used.

The weight ratio of phenolic or enolic compound(s) to transition metal chelator(s) is preferably from 1:20 to 2:1, especially from 1:10 to 1:1.

Optional Additional Components

A carrier material is a highly desired additional component of the products of the invention. The carrier material may be hydrophobic or hydrophilic, solid or liquid. Preferred carrier materials are liquids. Hydrophobic liquids suitable for use with the chelator salts of the invention include liquid silicones, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, or additionally, non-silicone hydrophobic liquids may be used. Such materials include mineral oils, hydrogenated polyisobutene, polydecene, paraffins, isoparaffins of at least 10 carbon atoms, aliphatic or aromatic ester oils (eg. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers.

Hydrophilic liquid carrier materials, for example water, may also be employed.

Particularly preferred liquid carrier materials comprise organic solvents. To aid compatibility between the chelator and the organic solvent, especially preferred organic solvents are relatively hydrophilic, having a c.logP of less than 2, especially −2 to 1, and in particular −0.5 to 0.5. c.logP is the calculated logarithm to the base 10 of the octanol:water partition coefficient; a method for calculating such values may be found in "Computer-assisted computation of partition coefficients from molecular structures using fragment constants", J.Chou and P.Jurs, *J. Chem. Inf. Comput. Sci.*, 19, 172 (1979). In addition, preferred organic solvents have a melting point of less than 10° C., preferably less than 5° C.; this can benefit both low temperature storage stability and ease of manufacture. A class of preferred organic solvents are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol (c.logP −1.538) propylene glycol (c.logP -1.06), butylene glycol (c.logP −0.728), ethanol (c.logP 0.235), propanol (c.logP 0.294), isopropanol (c.logP −0.074), and industrial methylated spirits. The most preferred organic solvents are aliphatic alcohols, in particular those having 2 to 3 carbon atoms, especially ethanol and isopropanol.

Mixtures of carrier materials may also be used. The amount of carrier material employed is preferably at least 5%, more preferably from 30% to 99%, and most preferably from 60% to 98% by weight of the composition, excluding any volatile propellant present.

When organic solvent is present in the composition, it is preferably present at from 30% to 98% by weight of the total weight of the liquid components of the composition; more preferably the organic solvent comprises from 60% to 97% by weight of the total liquids present.

For some compositions, notably roll-on and squeeze spray compositions, it is desirable to use an aqueous ethanol carrier material. In order to ease the attainment of product homogeneity, it is preferred that the ratio of ethanol to water in such compositions is from 1:1 to 2.5:1 and particularly from 1.5:1 to 2:1 by weight.

For some applications, it is desired that less than 50% by weight of water is present as part of the liquid components of the composition, more preferably less than 10%. For some preferred compositions, the ratio of other liquid components to water is between 95:5 and 99:1, by weight. In such compositions chelator salts having organic cations have particular solubility and compatibility advantages.

Preferred compositions with an organic solvent comprise a solution of the chelator in said organic solvent. Such solutions are preferably homogeneous, preferably having an absorbance, relative to the solvent, of less than 0.2, especially less than 0.1 (for a 1 cm pathlength at 600 nm) measured using a Pharmacia Biotech Ultrospec 200 Spectrophotometer or similar instrument.

Conventional organic anti-microbial agents may also be advantageously employed in the methods and products of the present invention. Levels of incorporation are preferably from 0.01% to 3%, more preferably from 0.03% to 0.5% by weight of the of the composition in which they are present, excluding any volatile propellant also present. Most of the classes of agents commonly used in the art can be utilised. Preferred additional organic anti-microbials are bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A.Makin and M. R.Lowry, in "Antiperspirants and Deodorants", Ed. K. Laden (1999, Marcel Dekker, New York). More preferred additional antimicrobials for use in the compositions of the invention are polyhexamethylene biguanide salts; 2',4,4'-trichloro,2-hydroxy-diphenyl ether (triclosan); and 3,7,11-trimethyldodeca-2,6,10-trienol (farnesol).

Inorganic anti-microbial agents may also be used in the compositions of the invention. Such materials can often function as anti-perspirant actives when present at a suitable concentration. Examples are often selected from astringent active salts, including, in particular, aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates. When included, preferred levels of incorporation are from 0.5% to 60%, particularly from 5% to 30% or 40% and especially from 5% or 10% to 30% or 35% by weight of the composition. Especially preferred aluminium halohydrate salts, known as activated aluminium chlorohydrates, are described in EP 6,739 (Unilever PLC and NV). Zirconium aluminium chlorohydrate actives are also preferred materials, as are the so-called ZAG (zirconium-aluminium-glycine) complexes, for example those disclosed in U.S. Pat. No. 3,792,068 (Procter and Gamble Co.). Zinc phenol sulphonate may also be used, preferably at up to 3% by weight of the composition.

Structurants and emulsifiers are further additional components of the compositions of the invention that are highly desirable in certain product forms. Structurants, when employed, are preferably present at from 1% to 30% by weight of the composition, whilst emulsifiers are preferably present at from 0.1% to 10% by weight of the composition. Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, quaternium-18 bentonite, quaternium-18 hectorite, silica, and propylene carbonate. Suitable emulsifiers are steareth-2, steareth-20, steareth-21, ceteareth-20, glyceryl stearate, cetyl alcohol, cetearyl alcohol, PEG-20 stearate, dimethicone copolyol, and poloxamines.

Further emulsifiers/surfactants desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers. Certain sensory modifiers are further desirable components in the compositions of the invention. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (eg. Aerosil 200), polyethylene (eg. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

Fragrance is also a desirable additional component in the compositions of the invention. Suitable materials include conventional perfumes, such as perfume oils and also include so-called deo-perfumes, as described in EP 545,556 and other publications. These latter materials may also qualify as aaditional organic anti-microbial agents. Levels of incorporation are preferably up to 4% by weight, particularly from 0.1% to 2% by weight, and especially from 0.7% to 1.7% by weight. Synergies can exist between the essential components the invention and certain fragrance components—long-lasting odour control being the result.

It should be noted that certain components of compositions perform more than one function. Such components are particularly preferred additional ingredients, their use often saving both money and formulation space. Examples of such components include ethanol, isopropyl myristate, and the many components that can act as both structurants and sensory modifiers, for example silica.

Further additional components that may also be included are colourants and preservatives, for example $C_1$–$C_3$ alkyl parabens.

When the present invention involves the use of an aerosol composition, a volatile propellant is an essential component of such composition. The level of incorporation of the volatile propellant is typically from 30 to 99 parts by weight, and particularly from 50 to 95 parts by weight. Non-chlorinated volatile propellant are preferred, in particular liquefied hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquefied hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane.

Other propellants that can be contemplated include alkyl ethers, such as dimethyl ether or compressed non-reactive gasses such air, nitrogen or carbon dioxide.

Methods of Manufacture

The details of the relevant methods of manufacture depend upon the product form concerned. However, for certain preferred compositions according to the invention, the method of manufacture involves the formation of a mixture of at least 0.35% by weight of a transition metal chelator and at least 0.05% by weight of a phenolic or enolic compound that is (a) a transferrin dissociation promoter that operates by aiding the reduction of iron(III) bound to transferrin to iron(II) and/or (b) an anti-oxidant comprising a tert-butylphenol group, wherein the weight percentages exclude any volatile propellant present.

EXAMPLES (Note that "letter" codes refer to Comparative Examples).
Preparation of Aerosol Deodorants Compositions The compositions detailed in Table 1 were prepared in the following manner.

0.50 g of DTPA was added as a powder to about 64 g of 96% (w/w) ethanol (exact amounts are in Table 1). To this mixture was added (dropwise, with stirring) 0.38 g of AMP. The resulting mixture was stirred, with gentle heating (50° C.) for 30 minutes. 0.33 g of isopropyl myristate was added to the resulting solution and mixed in, together with 0.10 g of BHT in the case of Example 1 and 0.05 g of BHT in the case of Example 2. The resulting mixture was sealed into a conventional aluminium deodorant can, having valve access, and 35 g (±0.2 g) of liquefied propellant (CAP 40, ex Calor) was introduced into the can from a propellant 'transfer can', via the valve, using a polyethylene transfer device. Finally, the can was fitted with a suitable actuator to enable effective spray application of the product.

Deodorancy Test 1

Anti-microbial compositions according to the current invention (Examples 1 and 2—see Table 1) and a control composition (Comparative Example A—see table 1) were prepared according to the method described. The deodorancy performances of the compositions were tested according to the following protocol. The results, presented in Table 1, illustrate the deodorancy benefit obtained from using compositions according to the invention.

Deodorancy Protocol

The panel employed comprised 50 individuals who had been instructed to use control ethanolic deodorant products during the week prior to the test. At the start of the test, panellists were washed with unfragranced soap and different products (1.20 g dose for aerosols or 0.30 g dose for roll-ons) applied to each axilla. (Product application was randomised to take into account any left/right bias). Panellists were instructed not to consume spicy food or alcohol, and not to wash under their own axillae, during the duration of the test. At least three expert assessors determined the intensity of axillary odour at set times (selected from 5 hours, 10 hours and 24 hours) after application, scoring the intensity on a scale of 1–5. After each 24 hour assessment, the panellists were re-washed, and products re-applied, as above. The procedure was repeated 4 times. At the end of the test the data were analysed using standard statistical techniques.

TABLE 1

DTPA-AMP/BHT vs. Control

| Component | Example 1 | Example 2 | Example A |
|---|---|---|---|
| DTPA (as free acid) | 0.50 | 0.50 | 0.50 |
| AMP | 0.38 | 0.38 | 0.38 |
| BHT | 0.1 | 0.05 | 0 |
| Isopropyl myristate | 0.33 | 0.33 | 0.33 |
| 96% Ethanol | 63.69 | 63.74 | 63.79 |
| CAP40[1] | 35 | 35 | 35 |
| Mean malodour intensity | 1.67 | 1.78 | 1.86 |

All components are expressed as weight percent of the total components added.
1. Propellant, proprietary mix of butane, isobutane and propane, ex. Calor.

The malodour intensities indicated were measured after 24 hours. The difference between the scores from Example 1 and Example A was significant at the 99% level. (Minimum difference required for significance: 0.17 at the 99% confidence level; 0.13 at the 95% confidence level).

Deodorancy Test 2

The deodorancy protocol described above was also used to test the performance of Examples 3 and B (see Table 2). These Examples were prepared in a similar manner to Examples 1 and A, with the modifications indicated in the Table.

TABLE 2

Fragranced DTPA-AMP/BHT vs. Fragranced Control

| Component | Example 3 | Example B |
|---|---|---|
| DTPA (as free acid) | 0.50 | 0 |
| AMP | 0.38 | 0 |

TABLE 2-continued

Fragranced DTPA-AMP/BHT vs. Fragranced Control

| Component | | Example 3 | Example B |
|---|---|---|---|
| BHT | | 0.1 | 0 |
| Isopropyl myristate | | 0.33 | 0.33 |
| 96% Ethanol | | 62.64 | 63.62 |
| CAP40 | | 35 | 35 |
| Fragrance | | 1.05 | 1.05 |
| Mean malodour | 5 hour | 1.04 | 1.20 |
| intensity | 24 hour | 1.48 | 1.99 |

All components are expressed as weight percent of the total components added.

The malodour differences between the compositions were significant at the 99% level, after both 5 hours and 24 hours. (Minimum differences required for significance at the 99% confidence levels were: 0.12 after 5 hours and 0.15 after 24 hours).

These results indicate that the deodorancy benefit of compositions of the invention is evident even in the presence of fragrance.

Deodorancy Test 3

The deodorancy protocol described above was also used to compare the performance of Example 1 with that of the comparative examples detailed in Table 3. The new comparative Examples were prepared in a similar manner to comparative example B.

TABLE 3

DTPA-AMP/BHT vs. Controls

| Component | | Example 1 | Example C | Example D |
|---|---|---|---|---|
| DTPA (as free acid) | | 0.50 | 0 | 0 |
| AMP | | 0.38 | 0 | 0 |
| BHT | | 0.1 | 0.1 | 0 |
| Isopropyl myristate | | 0.33 | 0.33 | 0.33 |
| 96% Ethanol | | 63.69 | 64.57 | 64.67 |
| CAP 40 | | 35 | 35 | 35 |
| Mean malodour | 5 hour | 1.81 | 1.93 | 2.04 |
| intensity | 10 hour | 1.77 | 2.19 | 2.26 |
| | 24 hour | 1.69 | 2.32 | 2.34 |

All components are expressed as weight percent of the total components added.

After 5 hours, the difference in mean malodour intensity between Example 1 and comparative Example D was significant at the 99% level. (Minimum differences required for significance: 0.17 at the 99% confidence levels; 0.13 at the 95% confidence level).

After 10 hours, Example 1 performance was significantly better than both comparative Examples at the 99% level. (Minimum differences required for significance: 0.18 at the 99% confidence levels; 0.14 at the 95% confidence level)

After 24 hours, Example 1 performance was significantly better than both comparative Examples at the 99% level. (minimum differences required for significance: 0.17 at the 99% confidence levels; 0.13 at the 95% confidence level)

It will be noted that no increase in odour was observed over the entire period of the test for the axillae to which Example 1 had been applied. It is also noteworthy that Example C (comprising BHT) did not perform significant better than the control (Example D).

Preparation of Roll-on Deodorants Compositions

EXAMPLE E

Control 1.0 g of DTPA (as the free acid) was added to ca. 25 g of water. The pH was adjusted to ca. 7.0 by dropwise addition of 0.76 g of AMP. Independently, 0.65 g of hydroxypropylcellulose (Klucel M, ex Aqualon) and 0.5 g of PEG-40 hydrogenated castor oil (Cremaphor RH40, ex BASF) were added to 70 g of ethanol, whilst shearing at a speed of ca. 8000 rpm on a Silverson L4RT mixer (ex. Silverson, Chesham, Bucks.), until a homogenous solution was obtained. The ethanolic solution was allowed to cool, mixed with the aqueous solution of DTPA/AMP, and the weight adjusted to 100 g with water.

EXAMPLE 4

1.0 g of DTPA (as the free acid) was added to ca. 25 g of water. The pH was adjusted to ca. 7.0 by dropwise addition of 0.76 g of AMP. Independently, 0.65 g of hydroxypropylcellulose (Klucel M, ex Aqualon) and 0.5 g of PEG-40 hydrogenated castor oil (Cremaphor RH40, ex BASF), and 0.25 g of 2,2'-ethylidenebis(4,6-di-tert-butylphenol) (Vanox 1290, ex Vanderbilt Co., Inc.) were added to 70 g of ethanol, whilst shearing at a speed of ca. 8000 rpm on a Silverson L4RT mixer (ex. Silverson, Chesham, Bucks.), until a homogenous solution was obtained. The ethanolic solution was allowed to cool, mixed with the aqueous solution of DTPA/AMP, and the weight adjusted to 100 g with water.

EXAMPLE 5

Prepared as Example 5, but with pentaerythritol tetrakis (3-(3,5-di-tert-butyl-4-hydroxyphenyl)propionate (Tinogard TT, ex Ciba Speciality Chemicals) used instead of Vanox 1290.

Deodorancy Test 4

The deodorancy protocol described above was also used to compare the performance of Examples 4 and 5 with that of comparative Example E. The results are presented in Table 4.

TABLE 4

Roll-on Deodorancy Performance

| Component | | Example 4 | Example 5 | Example E |
|---|---|---|---|---|
| DTPA (as free acid) | | 1.0 | 1.0 | 1.0 |
| AMP | | 0.76 | 0.76 | 0.76 |
| Vanox 1290 | | 0.25 | 0 | 0 |
| Tinogard TT | | 0 | 0.25 | 0 |
| Cremaphor RH40 | | 0.5 | 0.5 | 0.5 |
| Klucel M | | 0.65 | 0.65 | 0.65 |
| Ethanol (RR) | | 70 | 70 | 70 |
| Water | | 26.84 | 26.84 | 27.09 |
| Mean malodour | 5 hour | 1.56 | — | 1.95 |
| intensity | 24 hour | 1.80 | — | 2.25 |
| | 5 hour | — | 1.57 | 1.92 |
| | 24 hour | — | 1.90 | 2.22 |

All components are expressed as weight percent of the total components added.

Independent mean malodour intensity comparisons were made between Example 4 and comparative Example E and between Example 5 and comparative Example E. The results from the two tests cannot be directly compared.

On the test with Example 4, after 5 hours, the difference in mean malodour intensity between Example 4 and comparative Example E was significant at the 99% level. (Minimum differences required for significance: 0.14 at the 99% confidence levels; 0.11 at the 95% confidence level). Similarly, there was a 99% level of significant difference after 24 hours. (Minimum differences required for significance: 0.15 at the 99% confidence levels; 0.11 at the 95% confidence level).

On the test with Example 5, after 5 hours, the difference in mean malodour intensity between Example 5 and comparative Example E was significant at the 99% level. (Minimum differences required for significance: 0.14 at the 99% confidence levels; 0.11 at the 95% confidence level). Similarly, there was a 99% level of significant difference after 24 hours. (Minimum differences required for significance: 0.17 at the 99% confidence levels; 0.13 at the 95% confidence level).

Anti-microbial Performance Tests

The following test demonstrates the micromolar-active nature of DTPA and TTHA.

An axillary isolate of Staphylococcus epidermidis was grown overnight in 100 ml of tryptone soy broth (TSB, Oxoid Ltd). 10 ml of this culture was taken and subjected to centrifugation. The separated cells were re-suspended in 10 ml of phosphate buffered saline and the centrifugation procedure repeated. The washed cells were re-suspended in 10 ml of phosphate buffered saline to give the inoculum. 100 $\mu$l of the inoculum was added to 100 ml of semi-synthetic medium (SSM) containing $(NH_4)_2SO_4$ (0.066 g), $MgSO_4.7H_2O$ (0.012 g), KCl (0.1 g), $KH_2PO_4$ (0.27 g), $Na_2HPO_4$ (1.43 g), thiamin (0.1 mg), biotin (0.05 mg), Peptone P (0.05 g), and glucose (2.0 mmole) which had been previously sterilised by autoclaving at 121° C. for 20 minutes. The pH of the SSM was adjusted to 6.7 with HCl after sterilisation, prior to addition of the inoculum. This control medium was utilised in all of the in vitro inhibition studies. The chelator-containing test media were prepared in a similar manner, the chelator being introduced at a concentration of $3\times10^{-6}$ mol.dm$^{-3}$ before the pH adjustment with HCl.

100 $\mu$l of the S. epidermidis inoculum was introduced into the control medium and into test media containing the chelators indicated in Table 2. The cultures were inoculated at 37° C. (with agitation at 200 rpm) for 16 hours, and the optical density of the cultures measured at 600 nm to determine the extent of bacterial growth. By comparison of the optical density of the culture in the presence of chelating agent, to that of the control, the percentage inhibition of growth was established. (Optical density measurements were made on 1 in 4 dilutions of the cultures with 0.9% (w/v) saline, using 1 cm path length cuvettes, on a Pharmacia Biotech Ultrospec 200 Spectrophotometer.)

TABLE 4

Results of Anti-microbial Performance Tests

| Chelator | Inhibition of growth (%) |
| --- | --- |
| EDTA | 12.3 |
| CDTA | 0 |
| DTPA | 56.5 |
| TTHA | 56.3 |

Tranferrin Dissociation Promotion Test 2.7 g.l$^{-1}$ human diferric transferrin (ex Sigma Chemicals) was incubated at 37° C. in 50 mM HEPES (N-[2-hydroxyethyl]piperazine-N'-[2-ethanesulfonic acid]) buffer adjusted to pH 6.5 with sodium hydroxide, together with 0.115 g.l$^{-1}$ FerroZine (ex Sigma Chemicals; 3-(2-pyridyl)-5,6-bis(4-phenylsulfonic acid)-1,2,4-triazine, monosodium salt) and 10 mmol.l$^{-1}$ of the test material.

After 24 hours, the extent of transferrin dissociation was estimated spectrophotometrically by measuring absorption at 562 nm (vide supra). The data (see Table 5) illustrate the enhanced transferrin dissociation occurring in the presence of the indicated test materials.

TABLE 5

Transferrin Dissociation Promotion Results

| Test material | Absorption |
| --- | --- |
| None (Control) | 0.111 |
| Protocatechuic acid | 0.391 |
| Salicylic acid | 0.305 |
| Iron | 0.425 |

Further Compositions

The compositions shown in Tables 6 to 8 may be prepared by methods common in the art. The components are expressed as weight percent of the total components added.

TABLE 6

Squeeze Spray Compositions

| Component | Example 6 | Example 7 | Example 8 |
| --- | --- | --- | --- |
| Ethanol | 60 | 70 | 75 |
| DTPA | 1.0 | 0.45 | 0.35 |
| Fragrance | 1.2 | 1.3 | 1.2 |
| Sodium hydroxide | Sufficient to neutralise the DTPA | | |
| BHT | 0.05 | 0.1 | 0.2 |
| Glycerol | 1.0 | 1.0 | 1.0 |
| Water | To 100 | To 100 | To 100 |

TABLE 7

Further Roll-on Compositions

| Component | Example 9 | Example 10 | Example 11 |
| --- | --- | --- | --- |
| Ethanol | 55 | 60 | 65 |
| DTPA | 1.0 | 0.65 | 0.45 |
| Fragrance | 1.4 | 1.4 | 1.4 |
| Sodium hydroxide | 0.34 | 0.22 | 0.15 |
| BHT | 0.05 | 0.1 | 0.1 |
| Klucel M | 0.65 | 0.65 | 0.65 |
| Water | To 100 | To 100 | To 100 |

TABLE 8

Solid Compositions

| Component | Example 12 (Soft Solid) | Example 13 (Gel Stick) |
| --- | --- | --- |
| DTPA | 1.0 | 1.0 |
| BHT | 0.1 | 0.1 |
| Perfume | 1.0 | 1.2 |
| Dextrin Palmitate | 10 | 0 |
| Finsolv TN[1] | To 100 | 0 |
| Propylene Glycol | 0 | 22.5 |
| Dipropylene Glycol | 0 | 40.0 |
| Sodium Hydroxide | 0 | 1.325 |
| AMP | 0 | 0.4 |
| Sodium Stearate | 0 | 5.5 |
| Tetronic 1307[2] | 0 | 3.0 |
| Water | 0 | To 100 |

[1]C12–C15 alkyl benzoate, ex Finetex.
[2]Poloxamine 1307, ex BASF

What is claimed is:

1. A method of achieving an anti-microbial and deodorancy benefit comprising the application to the human body or to an article wearable in close proximity thereto, of an anti-microbial product comprising effective amounts of a transition metal chelator and a phenolic or enolic compound that is (a) a transferrin dissociation promoter that operates by aiding the reduction of iron(III) bound to transferrin to iron(II) and/or (b) an anti-oxidant comprising a tert-butylphenol group.

2. A method according to claim 1, comprising the application to the human body or to an article wearable in close proximity thereto, of a composition comprising at least 0.35% by weight of a transition metal chelator and at least 0.05% by weight of a phenolic or enolic compound, wherein the weight percentages exclude any volatile propellant present.

3. A method according to claim 1, wherein the transferrin dissociation promoter is capable of passing the following test:

2.7 g.l$^{-1}$ human diferric transferrin (ex Sigma Chemicals) is incubated at 37° C. in 50 mM HEPES (N-[2hydroxyethyl]piperazine-N'-[2-ethanesulfonic acid]) buffer adjusted to pH 6.5 with sodium hydroxide, together with 0.115 g.l$^{-1}$ FerroZine (ex Sigma Chemicals; 3-(2-pyridyl)-5,6-bis(4-phenylsulfonic acid)-1,2, 4-triazine, monosodium salt) and 10 mol.l$^{-1}$ of the test material, if water soluble, or 2.5 g.l$^{-1}$ of the test material, added as a finely ground powder, if water insoluble. After 24 hours, the extent of transferrin dissociation is estimated by eye or spectrophotometrically. Transferrin dissociation promoters lead a purple colouration; in particular, they lead to an absorption at 562 nm of 0.15 or 5 greater.

4. A method according to claim 1, wherein the phenolic or enolic compound comprises a tert-butyl phenol group.

5. A method according to claim 4, wherein the phenolic or enolic compound comprises a phenol group having two tert-butyl substituents.

6. A method according to claim 1, wherein the transition metal chelator is selected from diethylenetriaminepentaacetic acid (DTPA), triethylenetetraaminehexaacetic acid (TTHA), a salt of DTPA, a salt of TTHA, or any mixture of these transition metal chelators.

7. A method according to claim 1, wherein the transition metal chelator is a salt having an organic cation.

8. A method according to claim 1, wherein an additional conventional organic anti-microbial agent is utilised.

9. An anti-microbial deodorant composition for use on the human body comprising at least 0.35% by weight of a transition metal chelator and at least 0.05% by weight of a phenolic or enolic compound that is (a) a transferrin dissociation promoter that operates by aiding the reduction of iron(III) bound to transferrin to iron(II) and/or (b) an anti-oxidant comprising a tert-butylphenol group, wherein the weight percentages exclude any volatile propellant present.

10. A deodorant composition according to claim 9, wherein the phenolic or enolic compound is a transferrin dissociation promoter capable of passing the following test:

2.7 g.l$^{-1}$ human diferric transferrin (ex Sigma Chemicals) is incubated at 37° C. in 50 mM HEPES (N-[2-hydroxyethyl]piperazine-N'-[2-ethanesulfonic acid]) buffer adjusted to pH 6.5 with sodium hydroxide, together with 0.115 g.l$^{-1}$ FerroZine (ex Sigma Chemicals; 3-(2-pyridyl)-5,6-bis(4-phenylsulfonic acid)-1,2, 4-triazine, monosodium salt) and 10 mmol.l$^{-1}$ of the test material, if water soluble, or 2.5 g.l$^{-1}$ of the test material, added as a finely ground powder, if water insoluble. After 24 hours, the extent of transferrin dissociation is estimated by eye or spectrophotometrically. Transferrin dissociation promoters lead a purple colouration; in particular, they lead to an absorption at 562nm of 0.15 or greater.

11. A deodorant composition according to claim 9, wherein the phenolic or enolic compound comprises a tert-butyl phenol group.

12. A deodorant composition according to claim 11, wherein the phenolic or enolic compound comprises a phenol group having two tert-butyl substituents.

13. A deodorant composition according to claim 9, wherein the transition metal chelator is a salt having an organic cation.

14. A deodorant composition according to claim 9, also comprising an additional conventional organic anti-microbial agent.

15. A deodorant composition according to claim 9, wherein the transition metal chelator is selected from diethylenetriaminepentaacetic acid (DTPA), triethylenetetraaminehexaacetic acid (TTHA), a salt of DTPA, a salt of TTHA, or any mixture of these transition metal chelators.

16. A deodorant composition according to claim 9, wherein the transition metal chelator has a binding coefficient for iron(III) of greater than 102 .

17. A deodorant composition according to claim 12, wherein the phenolic or enolic compound is BHT.

18. A deodorant composition according to claim 9 that is an aerosol composition comprising a volatile propellant.

19. A deodorant composition according to claim 9 that is a roll-on or squeeze spray composition comprising ethanol and water at a ratio of between 1:1 and 2.5:1 by weight.

20. A deodorant composition according to claim 9 that is a cream, gel, soft solid, or solid stick composition comprising a thickener or structurant.

21. A method for the manufacture of a deodorant composition for use on the human body, comprising the formation of a mixture of at least 0.35% by weight of a transition metal chelator and at least 0.05% by weight of a phenolic or enolic compound that is (a) a transferrin dissociation promoter that operates by aiding the reduction of iron(III) bound to transferrin to iron(II) and/or (b) an anti-oxidant comprising a tert-butylphenol group, wherein the weight percentages exclude any volatile propellant present.

* * * * *